United States Patent [19]

Weyenberg et al.

[11] 4,145,001

[45] Mar. 20, 1979

[54] PACKAGING FOR CONTROLLED RELEASE OF VOLATILE SUBSTANCES

[75] Inventors: Robert J. Weyenberg; Don W. Seidler, both of Appleton, Wis.

[73] Assignee: American Can Company, Greenwich, Conn.

[21] Appl. No.: 833,500

[22] Filed: Sep. 15, 1977

[51] Int. Cl.² .............................................. A61L 9/04
[52] U.S. Cl. ....................................... 239/56; 53/478; 156/289; 156/290; 206/484.2; 428/43; 428/905
[58] Field of Search ................................. 239/53–57, 239/60; 206/484, 484.2, 524.2, 632; 428/43, 905; 156/289, 290; 53/39

[56] References Cited

U.S. PATENT DOCUMENTS

| | | | |
|---|---|---|---|
| 2,615,754 | 10/1952 | Lindenberg | 239/56 |
| 2,626,833 | 1/1953 | Valentine | 239/56 |
| 3,685,734 | 8/1972 | Paciorek et al. | 239/56 |
| 3,785,556 | 1/1974 | Watkins | 239/56 |
| 3,995,739 | 12/1976 | Tasch et al. | 206/484 |

*Primary Examiner*—Robert B. Reeves
*Assistant Examiner*—Michael J. Forman
*Attorney, Agent, or Firm*—Robert P. Auber; Ira S. Dorman; Harry C. Engstrom

[57] ABSTRACT

A package having plural layers with a quantity of volatile substance such as deodorizer sandwiched between the layers. The outer layers of the laminate are impermeable to the substance and its vapors, and thus prevent escape of the vapors as long as the package is sealed. Upon opening of the package, delamination occurs at the interface between two selected layers such that the volatile substance is covered on one side only by a layer of material which is permeable to the vapors, thereby allowing controlled release of the vapors over a period of time. A process for production of such packages is also disclosed.

26 Claims, 5 Drawing Figures

U.S. Patent  Mar. 20, 1979  4,145,001
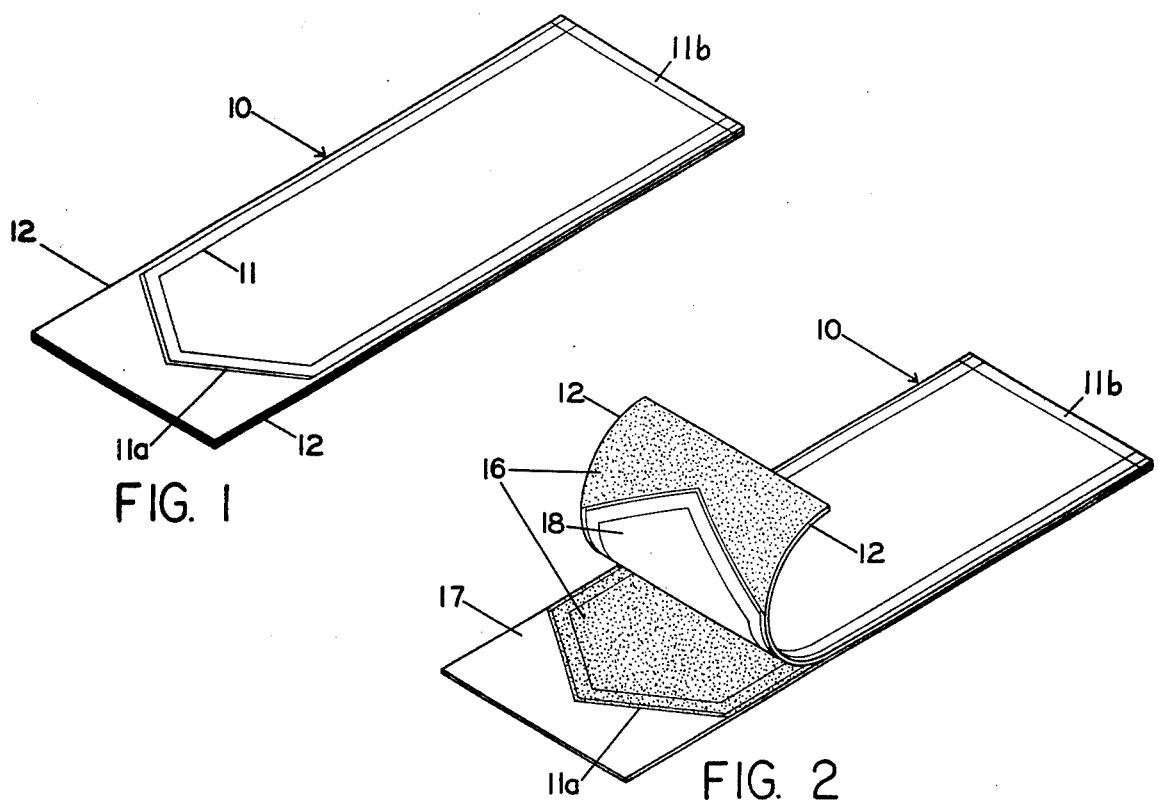
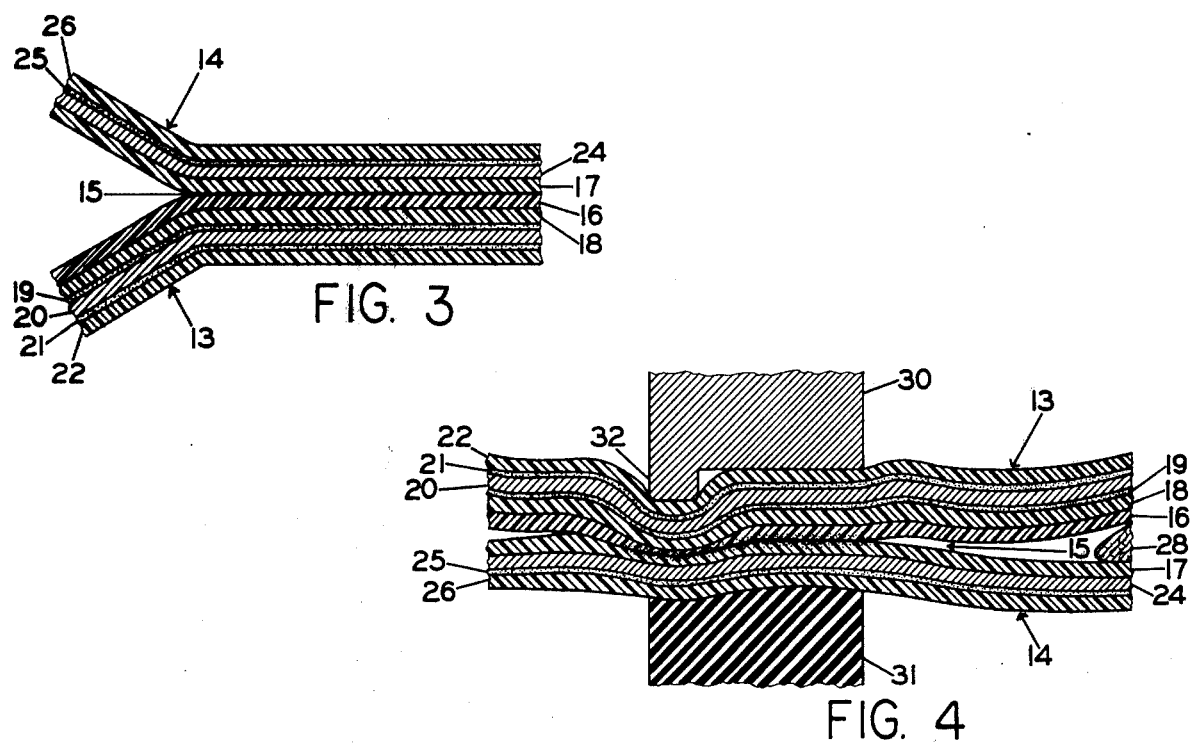

PACKAGING FOR CONTROLLED RELEASE OF VOLATILE SUBSTANCES

BACKGROUND OF THE INVENTION

1. Field of the Invention

This invention pertains generally to the field of packaging for volatile materials such as perfumes and deodorizers, and more particularly to packages which allow the controlled release of vapors over a period of time.

2. Description of the Prior Art

The controlled time release of very volatile substances such as perfumes and deodorizers presents a number of packaging problems. Room "air fresheners" or deodorizers have usually been packaged in glass bottles or vials, with the deodorizer being released into the atmosphere by transmission through an absorbant wick which is capped until the time of use. Many other common packaging materials including some plastic films are permeated by the vapors of the deodorizer, or are subject to attack by the deodorizer itself or by its liquid carrier. However, glass bottles are bulky and breakable, and generally it is not economical to package deodorizers in small quantities inside glass containers because of the cost of the container itself.

One proposed alternative method of packaging room deodorizers is to place a breakable glass vial within a plastic container formed of a material which is permeable to the vapors of the volatile deodorizer. The user deliberately breaks the glass vial to allow the deodorizer liquid to seep into an absorbant pad, and the vapors from the liquid slowly diffuse into the atmosphere through the permeable outer container. Such containers may be subject to accidental breakage of the glass vial during shipping and handling, as well as possible puncture of the container by broken glass, while the presence of the glass vial increases the manufacturing costs of such a container.

Other deodorant dispensers utilize sealed packages which are opened by peeling back a covering foil to expose a perforated panel covering an absorbant pad filled with the deodorizer. The costs of such containers makes them generally inappropriate for dispensing small amounts of deodorizer, while it is still somewhat difficult to obtain controlled release of the deodorizer at a fairly constant rate over the life of the product because of the direct exposure of the deodorizer liquid with the atmosphere.

SUMMARY OF THE INVENTION

This invention relates to a package for volatile substances such as room air fresheners, perfumes and deodorizers, which provides release of the vapors from the substance at a selected controlled rate over a period of time. The package has a plurality of layers of material laminated together, with a quantity of the volatile substance being sealed between two selected inner layers of the laminate. Because common volatile deodorizers or perfumes are usually in liquid form at room temperature an absorbant pad of gauze or paper is preferably used to carry the volatile liquid within the package. Outer layers of the laminate on either side of the volatile substance are selected to be impermeable to the liquid and its vapors, so that no vapors will escape as long as the package remains sealed.

The two inner layers are formed of thermoplastic material and are heat sealed together in a bond formed around the volatile substance. One of the inner layers is selected to be permeable to the vapors of the substance to allow controlled diffusion therethrough over a period of time, while the second layer is adhered to one of the outer layers of the package. A release layer is adhered to the permeable inner layer and to the second of the outer layers. The heat bonding around the volatile material is preferably accomplished by pressing all of the layers of the laminated package between a hot die and a resilient backing. In such a case, the release layer is selected of a material which will form only a weak heat bond with the permeable layer, the adhesion of which is substantially less than the adhesion of the heat bond between the permeable layer and the second inner layer, as well as being less than the adhesion of the bond between the second inner layer and the outer layer to which it is adhered. Preferably, the two inner layers are not adhered together except at the heat bond area, and thus the layers of the package can be easily pulled away from each other by the user between these layers up to the area of the bond. As the package is pulled by the user to the area of the heat bond, the permeable inner layer will split at the heat bond and remain bonded to the other inner layer, while the release layer will part from the permeable layer to allow the release layer and the outer layer adhered thereto to be peeled off. This leaves the volatile material covered on one side by only the permeable layer, such that vapors from the deodorizer will diffuse through the permeable layer into the atmosphere at a fairly constant rate over a period of time.

The process of heat bonding the layers of the package together is preferably accomplished using a die having a lip or protrusion extending slightly beyond the face of the remainder of the die. When such a die is pressed onto the laminated sheets and against a resilient backing, the thermoplastic inner layers will soften and spread apart from the line of the protrusion on the die to form a line of weakness. This line of weakness is advantageous in allowing the permeable layer to split easily as the package is peeled open by a user. To ensure the structural integrity of the package, it is preferable that the outer impermeable layers be formed of material which will not melt at the temperature of the bonding die.

For optimum performance of the package, it is also preferred that the line of weakness, and the wider heat bond adjacent to it, be formed in a V or chevron shape at a position spaced away from one end of the package. The user easily peels open the package up to the point of the chevron, with the weakened permeable layers splitting at the chevron to allow the remainder of the package to be peeled apart. The remainder of the heat seal surrounding the deodorizer pad is sealed over a broad area without forming a line of weakness. The provision of the line of weakness can be dispensed with where the cohesive integrity of the permeable layer is less than the adhesion of the bond formed between the permeable layer and the second inner layer, such that the permeable layer will be split along the initial line of the bond.

The package of this invention has the desirable feature of being relatively flat, light and has no breakable parts which could be dangerous, while being very inexpensive to manufacture and thus suitable for dispensing small quantities of deodorizer. As long as the package remains sealed, the volatile deodorizer can not escape, thus allowing very long shelf lives for the product. The construction of the package allows for dense packing of the product during transit, and easy handling. Special precautions during the handling of the product are unnecessary, since there are no parts that can be broken or easily damaged. Once the package has been opened by the consumer, the volatile vapors diffuse through the permeable layer at a controlled and selected rate. The material of the permeable layer can be "doped" with various impurities in an amount sufficient to increase the permeation rate to a selected desired rate. Because the process of transfer through the permeable layer is a diffusion process, rather than direct evaporation, the rate of release of vapor is relatively uniform over the expected life of the package.

In a preferred process for producing the package, the release layer and the permeable layer are preferably coextruded together to form a very uniform but weak bond between the two layers. One of the impermeable outer layers is then adhered to the release layer using an adhesive which provides a long lasting and uniform bond between the two materials. The other inner layer and the second outer layer are also strongly adhered together with the aid of an adhesive to form a laminate. The two laminates may then be brought together over an absorbant pad containing the volatile substance with a heated die being impressed over the two portions of the package to form a heat bond between them which surrounds the volatile material and seals in the vapors. Various materials such as metal foil may be used for the impermeable layer, and in such case it is desirable to protect the outer surface of the foil layers by adhering a tough protective layer thereto.

Further objects, features, and advantages of our invention will be apparent from the following detailed description taken in conjunction with the accompanying drawings showing preferred embodiments of our invention.

BRIEF DESCRIPTION OF THE DRAWINGS

In the drawings

FIG. 1 is an exterior perspective view of a package in accordance with our invention.

FIG. 2 is an exterior perspective view showing the package partially opened.

FIG. 3 is an expanded cross-sectional view of the two laminated panels of the package.

FIG. 4 is an expanded cross-sectional view of the package illustratively showing the bond formed by a heated die.

FIG. 5 is an expanded cross-sectional view of the package shown with the covering portion of the package removed to allow the vapors to diffuse into the atmosphere.

DESCRIPTION OF THE PREFERRED EMBODIMENTS

Referring to the drawings, a preferred embodiment of our package for selectively providing controlled release of vapors from a volatile substance is shown generally in an exterior view at 10 in FIG. 1. The package is shown in FIG. 1 in its unopened condition, in which the volatile deodorizer or perfume is sealed within the package. The embodiment of the package shown has a generally rectangular shape, and is relatively flat to allow easy storage and handling of the package. Because of the structure of the package, it can be quite severely bent or folded or otherwise manipulated without danger of accidentally opening the package and releasing the contents. An embossed heat seal strip 11 is visible on either surface of the package, and defines a peripheral band which surrounds the position of the volatile substance within the package. The package is opened by a user by pulling apart the package at corners shown generally at 12 where the package has not been heat sealed, and where there exists an interface between two of the layers of the package which have not been sealed together and which thus may be easily parted.

The structure of the package is best shown with reference to the cross-sectional view of FIG. 3, which pictorially illustrates the plurality of layers and their relationship in making up the laminated package. As described further below, the package is formed in two parts, having a first laminated panel 13 and a second laminated panel 14 which meet together at a joint or interface 15, with the volatile substance (not shown in FIG. 3) being interposed between the first and second panels. The two inner layers which meet at the interface 15 comprise a first inner layer 16 of thermoplastic material which is permeable to the vapors of the volatile substance, and a second inner layer 17 which is also formed of a thermoplastic material. The materials of which the layers 16 and 17 are formed are especially chosen to be capable of forming good heat seals to one another upon the application of moderate heat, preferably in the range of 200° to 600° F. Examples of materials which are satisfactory for forming the permeable layer 16 include high, medium, and low density polyethylene and ethylene vinyl acetate copolymer, as well as a number of other readily available polymer materials which are permeable to the particular deodorizer to be used. The aforementioned polymer materials are particularly adapted to the use of a deodorizer having an ethyl alcohol base. The degree of permeability of a particular polymer material can be increased by adding impurities such as calcium carbonate into the polymer material before the film is formed in order to open up additional spaces between the polymer chains. Additional permeability may also be a by-product of coloring the layer by introducing solid micro particles of pigment, which also tends to open up spaces between the polymer chains.

The second inner layer is chosen of a material that forms a good heat seal with the material of the permeable layer. For example, where low density polyethylene or ethylene vinyl acetate are used as the permeable layer, the second layer may advantageously be formed of ethylene acrylic acid copolymer which forms a strong heat seal bond with these materials. Other similar thermoplastics can also be utilized, such as ethylene vinyl acetate and low density polyethylene, and the second inner layer may be formed of the same material as the permeable layer. However, it is not necessary that the second inner layer be permeable to the vapors of the volatile material.

The permeable inner layer 16 is initially uniformly bonded to a release layer 18 which is composed of a material which does not form strong heat bonds with the permeable layer at the same temperatures at which bonds are formed between the two inner layers 16 and 17. For example, polypropylene can be utilized as the release layer in conjunction with a polyethylene or ethylene vinyl acetate permeable layer, in which case it is further desired to coextrude the permeable layer and release layer material together at a fairly low temperature to provide a very uniform but weak bond between the two film materials. The coextrusion of the films 16 and 18 is then laminated by an adhesive laminant 19 to a first vapor impermeable outer layer 20. For use with common perfumes and deodorizers, especially those having an alcohol base, the impermeable layer can be formed of metal foil such as aluminum foil, nylon films, and laminates of nylon and other polymer materials. Typically, the laminant layer 19 is formed of a hot melt of a polymer material which will adhere well to both the release layer and the impermeable layer. Such laminant materials include low density polyethylene, ethylene vinyl acetate, and ethylene acrylic acid copolymer.

The outer layer 20 has the primary function of preventing the escape of any of the volatile vapors from the interior of the package during the shelf life of the package. Where a foil material such as aluminum foil is used (which may be in the range of 0.0005 inch in thickness), it is desirable to protect the foil layer with a tough outer layer of polymer material. In particular, the outer layer 20 may be coated with a laminant 21 similar to the laminant 19, and a protective layer 22 may be adhered thereto. The protective layer can be formed of Mylar polyester, paper, cellophane, and various other polymer materials such as polypropylene.

In construction of the second laminated panel 14, the second inner layer 17 is adhered to a second outer layer 24 which is impermeable to vapors from the volatile material. The outer layer 24 is chosen of the same materials with the same considerations as the outer layer 20. Adherence of the second inner layer with the outer layer 24 may be obtained directly, such as by utilizing a strong adhering substance such as ethylene acrylic acid as the inner layer applied in hot melt to an aluminum foil outer layer. Where sufficient adhesion cannot be obtained in this manner, a laminant may be interposed between the inner layer and the foil layer to provide firm adhesion. It is important to the proper functioning of the package that the adhesion between the second inner layer 17 and the outer layer 24 be greater than the heat bond that is formed between the release layer 18 and the permeable layer 16, for the reasons that will be explained in further detail below. The outer layer 24 may also be protected, in which case a laminant layer 25 is used to secure an outer protective layer 26 thereto. The protective layer 26 may be formed in the same manner and of the same materials of the protective layer 22, and similarly the laminant 25 may be equivalent to the laminant used in the layer 21.

Referring to FIG. 4, an absorbant pad 28 carrying volatile deodorizer liquid is partially shown in place between the first and second laminated panels 13 and 14. The pictorial view of FIG. 4 illustrates the preferred method of sealing the layers of the package together around the pad 28 so as to prevent the escape of any vapors between the layers of the package. The layers of the package are shown as they are being heat sealed together between an upper heated metal die 30 and a lower resilient backing pad 31, which may also be heated. The die 30 shown in FIG. 4 is used to form the seal along the V or chevron, and has a protruding lip 32 formed on the front edge of the face thereof which extends beyond the remainder of the face for a short distance. The extension of the lip 32 is generally chosen to be no greater than the thickness of the package itself, and is preferably in the range of 4 to 5 thousandths of an inch. Because the die 30 and the backing pad 31 are heated, the thermoplastic layers within the package will melt and adhere together when the die and backing pad are pressed over them for a sufficient period of time. The heat bond formed between the inner thermoplastic layers 16 and 17 is very strong and will not be delaminated by the volatile liquid in the pad. Moreover, because the bond is formed with a substantial width, there will be relatively little escape of vapors by lateral permeation through the permeable layer 16.

As described above, the heat seal illustrated at 11 in FIGS. 1 and 2 is formed to surround the volatile substance. However, it is not necessary that the entire bond be formed at the same time. For example, the V-shaped front and long sides of the bond could be formed initially. A pad containing the volatile substance could then be placed in the pocket formed between the panels 13 and 14, and an end seal 11b could then be formed to complete the seal. It is apparent that liquid deodorizer can be deposited directly in the initially formed pocket and then sealed in, thus eliminating the need for a carrier pad.

The die portion 30 shown in FIG. 4 is used to provide the initial V-shaped bond at a position spaced laterally away from one of the edges of the package. The portion of the die used to provide the heat bond along the sides of the package and at the other end would preferably be formed flat and have no protruding lip since it is not necessary to form lines of weakness in the bonds along these sides. Such a line of weakness 11a is formed in the thermoplastic layer 16 by the action of the protruding lip 32, since the fluid thermoplastic thins out underneath the lip 32 and bulges out to the sides of the lip. The permeable layer 16 is thus very thin along the line directly under the lip 32. When the packages are pulled apart between the layers 16 and 17, the permeable layer 16 will split at the line of weakness 11a but will remain adhered to the underlying inner layer 17 because of the strong heat bonds formed between these layers under the flat portion of the die 30. The top layers 18, 19, 20, 21 and 22 will thus be pulled off, leaving only the permeable layer 16 covering the absorbant pad 28. This result is shown pictorally in the cross-sectional view of FIG. 5. The pad 28 is thus completely sealed arund its sides but the volatile vapors from the pad can escape by diffusing through the permeable layer 16 to the atmosphere.

The following examples are provided as illustrative of the invention, but should not be construed as being exhaustive or as limiting the invention to the specific details thereof.

EXAMPLE 1

A base for the permeable layer was formed of a mixture of 87% by weight low density polyethylene resin, 8% calcium carbonate, and 5% particulate green pigment. The pigmented polyethylene blend was hot melted and cast coextruded at approximately 420° F. with a release film consisting of ¼ mil propylene copolymer and ¼ mil polypropylene. The polyethylene blend was cast to a thickness of 1 ¼ mil.

Two outer impermeable layers were identically formed of sheets of 0.00035 inch thickness aluminum foil with 48 gauge Mylar polyester laminated on the outside surface thereof utilizing a hot melted seven pounds per ream (one ream equals 3,000 square feet) low density polyethylene laminant. The second inner layer of ethylene acrylic acid copolymer was hot melt case on the bare aluminum side of one of the coated foil outer layers to a weight of 14 pounds per ream. The coextrusion of the release layer and permeable layer was then adhered by the release layer side to the other coated foil using a laminant of hot melted 7 pound per ream low density polyethylene.

A seal was formed between the permeable layer and the ethylene acrylic acid layer by pressing the layers between a hot die and a heated rubber backing on the bottom, using a die temperature of approximately 320° F. applied for a sufficient period of time for the heat bonds to form (approximately 1 second). The package was initially sealed with a chevron shaped front edge and along the sides of the package to form a pocket. An absorptive paper pad soaked with an ethyl alcohol based deodorizer was placed in the pocket and the open end was heat sealed.

Several packages formed in this manner were sized to 2 ¾ inches width by 7 inches. The dies forming the heat bond provided a uniform 3/16 inch wide bond, and with a 0.021 inch by 1/6 inch wide raised surface formed as the leading edge of the chevron shaped top die to a height of 5 mils.

After the sealed packages were cleaned, there was substantially no odor emanating from the packages, indicating that no leakage was taking place through the seals. Upon opening of the packages, by pulling the top and bottom panels apart between the two inner layers, the permeable inner layer of pigmented polyethylene split apart uniformly along the line of weakness in a V-shape and remained adhered to the second inner layer. The deodorizer perfume odor could easily be detected, and a substantially constant odor level was observed for a period of approximately 7 days after opening.

EXAMPLE 2

A base material for the permeable layer was formed of 87% low density polyethylene resin, 8% calcium carbonate, and 5% solid particulate pigment. The polyethylene blend was hot melted and coextruded at a temperature of 420° F. with polypropylene, with the polyethylene layer having a 1 ½ mil thickness and the polypropylene layer having a ¼ mil thickness. Two outer impermeable layers were formed by laminating 50 gauge Mylar polyester with 7 pounds per ream low density polyethylene laminant to 0.0005 inch thickness aluminum foil. 15 pounds per ream ethylene acrylic acid was extruded onto the bare side of one of the foil layers, and the polyethylene-polypropylene coextrusion was adhered onto the bare side of the other foil layer using 7 pounds per ream low density polyethylene as a laminant. An absorptive paper pad filled with alcohol based perfume was sealed between the two structures using the sealing die and method set forth in Example 1 above. The two panels of the package were pulled apart and the polyethylene permeable layer again split along the V-shaped leading edge of the heat seal and delaminated from the polypropylene to leave only the polyethylene layer covering the perfumed pad. Release of perfume odors was detected for a period of approximately 7 days after opening.

EXAMPLE 3

The base material for the permeable layer was formed of ethylene vinyl acetate resin forming 87% of the mixture with 5% green particulate pigment and 8% calcium carbonate added. The pigmented resin mixture was hot melted and extrusion cast at 400° F. with polypropylene to form a laminate having ¼ mil polypropylene as the release layer and 1 ¼ mil of the ethylene vinyl acetate mixture as the permeable layer.

The outer impermeable layers were formed by coating 0.00035 inch aluminum foil with 48 gauge Mylar polyester using hot melted low density polyethylene at a thickness of 7 pounds per ream as the adhesive. Ethylene acrylic acid copolymer was hot melt cast on the bare aluminum side of one of the outer layers to a thickness of 15 pounds per ream. The polypropylene side of the coextrusion was adhered to the bare aluminum side of the other of the coated foil outer layers using hot melted low density polyethylene at 7 pounds per ream as an adhesive.

A thin absorptive paper pad was filled with alcohol based perfume, and a heat seal was formed around the pad as described in Example 1 above. Very little odor from the perfume was observed while the packages were sealed. The package was opened by pulling it apart between the unsealed portions, and the ethylene vinyl acetate permeable layer was observed to split at the point of weakness along the leading edge of the chevron shaped bond and thereafter delaminate from the polypropylene to leave a single layer of ethylene vinyl acetate covering the perfume soaked pad. Significant detectable odor was observed from all packages identically made as described above for periods between 7 and 14 days.

EXAMPLE 4

A permeable film base mixture was formed of 85% ethylene vinyl acetate resin, 10% calcium carbonate, and 5% particulate green pigment. This mixture was hot melted and cast coextruded with polypropylene as the release layer to a thickness of ¼ mil polypropylene and 1 mil ethylene vinyl acetate mixture.

Outer impermeable layers were formed by adhering 48 gauge Mylar polyester to 0.00035 inch foil using 7 pounds per ream low density polyethylene as an adhesive. On the bare aluminum side of one of the outer layers, ethylene acrylic acid polymer was coated to a density of 15 pounds per ream. The bare aluminum side of the other outer layer was coated with a maleic anhydride modified polypropylene primer, available from Morton Chemical Company under the name Morprime, to a thickness of 1 pound per ream after drying.

The polypropylene side of the laminated release film and permeable film was adhered to the primed foil as prepared above using 10 pounds per ream polypropylene resin as an adhesive laminant.

The two laminated portions of the package were then sealed over a paper pad soaked with alcohol based perfume using the sealing method described above in Example 1.

Several packages produced above were opened by peeling back the parts of the package that had not been laminated together, and a splitting of the ethylene vinyl acetate permeable layer was observed to take place at the line of weakness formed on the front of the chevron shaped bond, with the permeable layer thereafter adhering to the second inner layer and delaminating from the polypropylene release layer. Evolution of odor from the covering permeable layer occurred in all of the packages for periods from 7 to 14 days. The addition of the primer in the bond formed between the foil and the polypropylene release layer aided in making this bond stronger and more resistant to attack by the alcohol perfume carrier over the expected shelf life of the packages.

It has been found that it is desirable to form a very uniform but weak bond between the release layer and the permeable layer to allow proper delamination between these layers when the package is pulled apart. Preferably, the strength of these bonds will be in the range of 50 to 75 grams per inch, as tested on an Instron tester at 180° with a free tail at 10 inches per minute. The bond is preferably uniform to prevent the perfume and alcohol from seeping through the permeable layer and forming pockets between the permeable layer and the release layer. Such pockets of perfume could produce unwanted excess discharge of perfume or deodorizer when the package is initially opened. The case coextrusion process has been found to provide such a desirable bond between the common materials utilized for the two layers, such as polyethylene or ethylene vinyl acetate for the permeable layer and polypropylene for the release layer. For such a case, it is then found that it is most desirable to maintain the temperature of the hot melt of the mixes going into the coextruder at 400° F. to 420° F., as opposed to the higher temperatures normally used to provide coextrusions between these materials.

It is understood that the invention is not confined to the particular embodiments herein described as illustrative of the invention, but embraces all such modifications thereof as come with the scope of the following claims.

We claim:

1. A package selectively providing controlled release of vapors from a volatile substance, comprising:
   (a) first and second outer layers of material impermeable to the vapors of the volatile substance;
   (b) first and second inner layers of thermoplastic material sealed together in a bond formed around a quantity of the volatile substance, the first of said layers being permeable to the vapors of the volatile substance and the second of said layers being adhered to one of said outer layers;
   (c) a release layer adhered to said permeable inner layer and to the other of said outer layers, the adhesion of said release layer to said permeable layer being less than the adhesion of the bond between said inner layers, less than the adhesion between said release layer and said outer layer adhered thereto, and less than the adhesion between said second inner layer and said outer layer adhered thereto, and wherein the cohesion of said permeable layer at the bond is less than its adhesion to said second inner layer, whereby when a user pulls the package apart by pulling apart the portions of the package where said inner layers are not bonded, said permeable layer will pull apart at the bond and will remain adhered to said second inner layer and will delaminate from said release layer, such that the volatile substance will be covered only by said permeable layer to allow the diffusion of vapors from the volatile substance therethrough at a selected controlled rate over a period of time.

2. The package of claim 1 wherein the bond between said inner layers is formed by a heat seal between said layers.

3. The package of claim 1 wherein a portion of the bond is spaced away from one edge of the package and is formed in a V-shape with the point of the V facing said one edge of the package to thereby facilitate the splitting of said permeable layer at the V-shaped portion of the bond.

4. The package of claim 1 wherein at least said permeable layer is spread apart and thinned along a portion of the bond which is spaced away from one edge of the package to form a line of weakness in said permeable layer which splits easily upon opening of the package.

5. The package of claim 4 wherein the edge of the bond portion that has the line of weakness formed thereof is formed in a V-shape with the point of the V facing the one edge of the package.

6. The package of claim 1 wherein the material of said permeable layer is selected from the group consisting of polyethylene and ethylene vinyl acetate copolymer.

7. The package of claim 6 wherein the resin of which said permeable layer is formed is uniformly intermixed with calcium carbonate in an amount sufficient to provide a selected permeation rate through said permeable layer.

8. The package of claim 1 wherein said second inner layer consists essentially of ethylene acrylic acid copolymer.

9. The package of claim 1 wherein the material of said release layer is selected from the group consisting of polypropylene, nylon, propylene copolymer, and a coextrusion of polypropylene and propylene copolymer.

10. The package of claim 1 wherein the material forming said impermeable layers is selected from the group consisting of aluminum foil and nylon.

11. The package of claim 1 wherein the material of said impermeable layers is aluminum foil and wherein a layer of protective material is adhered to the outside surfaces of said aluminum foil layers.

12. The package of claim 11 wherein the protective material layer is selected from the group consisting of polyesters, paper, cellophane, and polypropylene.

13. The package of claim 1 wherein the volatile substance between said inner layers is an ethyl alcohol based deodorizer absorbed in a paper pad.

14. A process for producing a package which provides selective controlled release of vapors from a volatile substance, comprising the steps of:
   (a) laminating together a release layer and a permeable inner layer at a selected adhesive strength between the two layers, said permeable layer being formed of a thermoplastic material which is permeable to the vapors of the volatile substance;
   (b) laminating the release layer side of the release layer-permeable layer laminate to a first outer layer to form a first laminated panel, the outer layer being formed of a material which is impermeable to the vapors of the volatile substance, the adhesion between the release layer and the impermeable layer being greater than the adhesion between the release layer and the permeable layer;
   (c) laminating a second inner thermoplastic layer onto a second impermeable layer to form a second laminated panel, the adhesion between the second inner layer and the second impermeable layer being greater than the adhesion between the permeable layer and the release layer of the first panel;
   (d) placing the first and second panels together over a quantity of the volatile substance with the permeable layer and the second inner layer in facing relation;
   (e) forming a heat bond between the first and second panels with the bond surrounding the quantity of volatile substance, the heat bond being formed such that the adhesion of the release layer to the permeable layer is less than the adhesion of the bond between the permeable layer and the second inner layer, less than the adhesion between the release layer and the impermeable layer adhered thereto, and less than the adhesion between the second inner layer and the impermeable layer which is adhered thereto.

15. The process of claim 14 wherein the step of heat bonding the first and second panels together consists of pressing together the first and second panels between a heated upper die having the outer shape of the desired heat bond and a lower resilient heated backing.

16. The process of claim 15 wherein one of the edges of the die is spaced away from one edge of the package and has a protruding lip along the outside edge thereof, such that when said upper die and lower backing are pressed together over the first and second panels the protruding lip causes the thermoplastic inner layers to melt and spread apart to form a line of weakness in the package, whereby when the package is opened by a user, the thermoplastic permeable layer will split at the line of weakness and will delaminate from the release layer and remain bonded to the layers of the second panel.

17. The process of claim 16 wherein the die portion having the protruding lip thereon is formed in the shape of a V with the point of the V facing the one edge of the package which the heat bond is spaced away from.

18. The process of claim 14 wherein the permeable layer is formed of a material selected from the group consisting of polyethylene and ethylene vinyl acetate.

19. The process of claim 18 wherein the resin of which the permeable layer is formed is uniformly intermixed with calcium carbonate in an amount sufficient to provide a selected permeation rate through the permeable layer.

20. The process of claim 14 wherein the second inner layer is formed of a material which consists essentially of ethylene acrylic acid copolymer.

21. The process of claim 14 wherein the material of which the release layer is formed is selected from the group consisting of polypropylene, nylon, propylene copolymer, and a coextrusion of polypropylene and propylene copolymer.

22. The process of claim 14 wherein the impermeable layers are formed of a material selected from the group consisting of aluminum foil and nylon.

23. The process of claim 14 wherein the impermeable layers are formed of aluminum foil and including the additional step of adhering a layer of protective material to the outside surfaces of each of the aluminum foil layers.

24. The process of claim 23 wherein the protective material layer is formed of a material selected from the group consisting of polyesters, paper, cellophane, and polypropylene.

25. The process of claim 14 wherein the volatile substance emplaced between the permeable layer and the second inner layer is an ethyl alcohol based deodorizer absorbed in a paper pad.

26. The process of claim 14 wherein the step of forming a heat bond between the first and second panels includes the steps of partially bonding the panels together to form a pocket open at one end of the package, and then bonding the open end of the package after a quantity of the volatile substance has been placed in the pocket to completely seal in the volatile substance.

* * * * *